(12) United States Patent
Nguyen

(10) Patent No.: US 10,112,760 B2
(45) Date of Patent: Oct. 30, 2018

(54) PACKAGED ORAL CARE IMPLEMENT AND PACKAGE

(71) Applicant: COLGATE-PALMOLIVE COMPANY, New York, NY (US)

(72) Inventor: Quang Nguyen, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 137 days.

(21) Appl. No.: 15/344,509

(22) Filed: Nov. 5, 2016

(65) Prior Publication Data

US 2017/0050791 A1 Feb. 23, 2017

Related U.S. Application Data

(62) Division of application No. 14/238,168, filed as application No. PCT/US2011/047794 on Aug. 15, 2011, now Pat. No. 9,505,540.

(51) Int. Cl.

| | |
|---|---|
| *B65D 83/10* | (2006.01) |
| *B65D 75/58* | (2006.01) |
| *B65D 75/36* | (2006.01) |
| *B65D 75/56* | (2006.01) |
| *A46B 9/04* | (2006.01) |
| *A61C 17/34* | (2006.01) |
| *A61C 17/20* | (2006.01) |

(52) U.S. Cl.
CPC ............ *B65D 75/5833* (2013.01); *A46B 9/04* (2013.01); *A61C 17/20* (2013.01); *A61C 17/34* (2013.01); *B65D 75/366* (2013.01); *B65D 75/367* (2013.01); *B65D 75/563* (2013.01); *B65D 75/566* (2013.01); *A61C 2202/00* (2013.01); *B65D 2575/367* (2013.01)

(58) Field of Classification Search
CPC .... B65D 17/163; B65D 17/168; B65D 17/24; B65D 5/747; B65D 2101/0023; B65D 75/58; B65D 75/5805; B65D 75/5827; B65D 75/5838; B65D 75/5844; B65D 75/585; B65D 75/5833; B65D 75/367; B65D 75/366; B65D 75/563; B65D 75/566; B65D 2575/367; A46B 9/04; A61C 19/02; A61C 2202/00
USPC ............ 206/368, 361, 209, 234, 703, 362.2, 206/362.1, 531, 63.5, 824, 815, 804, 206/521.15, 462, 581, 532, 459.5, 469; 220/270, 266, 282, 265, 277, 278, 602, 220/662, 276, 260; 15/105, 106, 167.1
See application file for complete search history.

(56) References Cited

U.S. PATENT DOCUMENTS

| | | |
|---|---|---|
| 3,689,458 A | 9/1972 | Hellstrom |
| 3,942,640 A | 3/1976 | Hellstrom |

(Continued)

FOREIGN PATENT DOCUMENTS

CH 619 409 9/1980

OTHER PUBLICATIONS

International Search Report and the Written Opinion issued in International Application PCT/US2011/047794 dated May 2, 2012.

*Primary Examiner* — Rafael Ortiz

(57) ABSTRACT

A packaged oral care implement and a package having an easy-open feature. In one embodiment, the invention utilizes a protuberance that acts as a fulcrum to force an edge of a tear-away portion to protrude from a surface of the package in response to a force being applied to a force-application area of the tear-away portion.

13 Claims, 8 Drawing Sheets

(56) References Cited

U.S. PATENT DOCUMENTS

| | | | |
|---|---|---|---|
| 4,191,293 A | 3/1980 | Newman | |
| 4,371,095 A | 2/1983 | Montgomery | |
| 4,607,768 A * | 8/1986 | Taber | B65D 47/0847 |
| | | | 215/237 |
| 5,004,110 A | 4/1991 | Osip | |
| 5,033,616 A | 7/1991 | Wyser | |
| 5,215,381 A | 6/1993 | Wade | |
| 5,551,564 A | 9/1996 | Prater et al. | |
| 5,711,448 A | 1/1998 | Clarke, III | |
| 6,283,333 B1 * | 9/2001 | Knickerbocker | B65D 47/2006 |
| | | | 222/153.14 |
| 8,042,689 B2 | 10/2011 | Frojd et al. | |
| 2002/0162764 A1 | 11/2002 | Sherline et al. | |
| 2004/0062493 A1 | 4/2004 | Ishigami et al. | |
| 2004/0074917 A1 | 4/2004 | McHutchinson | |
| 2004/0182739 A1 | 9/2004 | Williams-Hartman | |
| 2004/0206253 A1 | 10/2004 | Filion | |
| 2004/0241130 A1 | 12/2004 | Tamareselvy | |
| 2005/0145519 A1 | 7/2005 | Fattori | |
| 2005/0167311 A1 | 8/2005 | Tonsfeldt et al. | |
| 2005/0218027 A1 | 10/2005 | Lammers et al. | |
| 2006/0027480 A1 | 2/2006 | Buss | |
| 2006/0096887 A1 | 5/2006 | Morrison | |
| 2006/0249422 A1 | 11/2006 | Bates, Jr. | |
| 2007/0012592 A1 | 1/2007 | Bertsch et al. | |
| 2007/0023382 A1 | 2/2007 | Sandberg | |
| 2007/0023884 A1 | 2/2007 | Branzell et al. | |
| 2007/0045154 A1 | 3/2007 | Gelardi et al. | |
| 2007/0068844 A1 | 3/2007 | Weston | |
| 2007/0102317 A1 | 5/2007 | Crawford et al. | |
| 2007/0256307 A1 | 11/2007 | Mann | |
| 2007/0272586 A1 | 11/2007 | Hession | |
| 2008/0029418 A1 | 2/2008 | Calendrille, Jr. | |
| 2008/0038046 A1 | 2/2008 | Jalili | |
| 2008/0173564 A1 | 7/2008 | Aldridge et al. | |
| 2008/0314791 A1 | 12/2008 | Schweitzer et al. | |
| 2009/0090643 A1 | 4/2009 | Fischer et al. | |
| 2009/0134054 A1 | 5/2009 | Lee et al. | |
| 2009/0184023 A1 | 7/2009 | Brollier et al. | |
| 2010/0018974 A1 | 1/2010 | Lyzenga et al. | |
| 2010/0059401 A1 | 3/2010 | Schein et al. | |
| 2010/0102062 A1 | 4/2010 | Jones et al. | |
| 2010/0230312 A1 | 9/2010 | Sorrentino et al. | |
| 2010/0252478 A1 | 10/2010 | Beecroft et al. | |
| 2010/0314279 A1 | 12/2010 | Hansen et al. | |
| 2011/0042262 A1 | 2/2011 | Naik et al. | |
| 2011/0068044 A1 | 3/2011 | Sorrentino et al. | |
| 2011/0100845 A1 | 5/2011 | Meech et al. | |
| 2011/0121010 A1 | 5/2011 | Loftin et al. | |
| 2012/0145567 A1 * | 6/2012 | Nguyen | B65D 75/326 |
| | | | 206/63.5 |
| 2014/0008266 A1 * | 1/2014 | Lee | B65D 75/368 |
| | | | 206/581 |

\* cited by examiner

PACKAGED ORAL CARE IMPLEMENT AND PACKAGE

CROSS-REFERNCE TO RELATED PATENT APPLICATIONS

The present application is a divisional of U.S. application Ser. No. 14/238,168, filed Feb. 10, 2014, which is a U.S. national stage under 35 U.S.C. § 371 of PCT Application No. PCT/US2011/047794, filed Aug. 15, 2011, the entireties of which are incorporated herein by reference.

FIELD OF THE INVENTION

The present invention relates generally to the field of packaging, and specifically to packaged oral care implements having an easy-open feature.

BACKGROUND OF THE INVENTION

In the commercialization of toothbrushes, the current trend is to package toothbrushes in blister packages. While the use of blister packages has proved to be cost-effective and effective at adequately protecting the toothbrush contained therein, existing blister packages are often difficult to open. While easy-open blister packages have been introduced into the art, existing easy-open blister packages are either complex to manufacture and/or compromise the containment of the product. Still a further issue with existing easy-open blister packages is that sharp protruding edges may be exposed that can prevent shipping, cause inadvertent opening, and/or injury to the end user. Thus, a need exists for an improved easy-open blister package that eliminates one or more of the aforementioned deficiencies.

BRIEF SUMMARY OF THE INVENTION

The present invention is directed to a blister package having an easy-open feature that utilizes a tear-away portion formed into a panel of the blister package. An edge of the tear-away portion can be manipulated from a position in which it either does not protrude (or protrudes slightly) from the panel to a position where the edge protrudes (or protrudes a greater distance) from the panel so as to facilitate easy grasping. The manipulation of the edge of the tear-away portion from is effectuate by application of a force to a specific area of the tear-away portion that causes a protuberance to act as a fulcrum that lifts the edge of the tear-away portion from the non-protruding position to the protruding position.

In one embodiment, the invention can be a packaged oral care implement comprising: a blister package having a receiving cavity; an oral care implement positioned within the receiving cavity; the blister package comprising a panel, the panel comprising a tear-away portion and a base portion, the tear-away portion comprising an edge lying substantially flush with the base portion, a protuberance extending from an inner surface of the tear-away portion, and a force-application area, the protuberance located between the edge and the force-application area; and the edge protruding outwardly from the base portion when a force is applied to the force-application area as a result of the protuberance acting as a fulcrum.

In another embodiment, the invention can be a package comprising: a body forming a receiving cavity; the body comprising a panel, the panel comprising a base portion and one or more pre-weakened lines or cuts that define a tear-away portion, the tear-away portion comprising an edge and a force-application area; and a protuberance located between the edge and the force-application area of the tear-away portion; wherein the edge of the tear-away portion: (1) does not protrude from the base portion when force is not applied to the force-application area; and (2) protrudes outwardly from the base portion when a force is applied to the force-application area as a result of the protuberance acting as a fulcrum.

In yet another embodiment, the invention can be a method of opening a packaged product comprising: providing an product disposed within a receiving cavity of a blister package, the blister package comprising a panel, the panel comprising a base portion and one or more pre-weakened lines or cuts that define a tear-away portion, the tear-away portion comprising an edge that does not protrude from the base portion, a protuberance extending from an inner surface of the tear-away portion; applying a force to an outer surface of the tear-away portion to cause the edge to protrude outwardly from the base portion as a result of the protuberance acting as a fulcrum; and grasping the protruding edge of the tear-away portion and at least partially separating the tear-away portion from the base portion to provide access to the product.

In a further aspect, the invention can be a package comprising: a body forming a receiving cavity; the body comprising a panel, the panel comprising a base portion and one or more pre-weakened lines or cuts that define a tear-away portion, the tear-away portion comprising an edge and a force-application area; and a protuberance located between the edge and the force-application area; wherein the edge of the tear-away portion: (1) protrudes outwardly from the base portion a first distance when force is not applied to the force-application area; and (2) protrudes outwardly from the base portion a second distance when a force is applied to the force-application area as a result of the protuberance acting as a fulcrum, the second distance being greater than the first distance.

In a yet further aspect, the invention can be a packaged oral care implement comprising: a blister package comprising a receiving cavity; a panel, the panel comprising a tear-away portion and a base portion, the tear-away portion comprising an edge protruding outwardly a first distance from the base portion; a protuberance extending from an inner surface of the tear-away portion; and the edge protruding outwardly a second distance front the base portion when a force is applied to an outer surface of the tear-away portion as a result of the protuberance acting as a fulcrum, the second distance greater than the first distance. The packaged oral care implement further comprising an oral care implement positioned within the receiving cavity.

In an even further aspect, the invention can be a method of opening a packaged product comprising: providing a product disposed within a receiving cavity of a blister package, the blister package comprising a panel, the panel comprising a base portion and one or more pre-weakened lines or cuts that define a tear-away portion, the tear-away portion comprising an edge that protrudes outwardly a first distance from the base portion and a force-application area, a protuberance located between the edge and the force-application area; applying a force to the force-application area of the tear-away portion to cause the edge to protrude outwardly a second distance from the base portion as a result of the protuberance acting as a fulcrum, the second distance greater than the first distance; and grasping the protruding edge of the tear-away portion and at least partially separating the tear-away portion from the base portion to provide access to the product.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
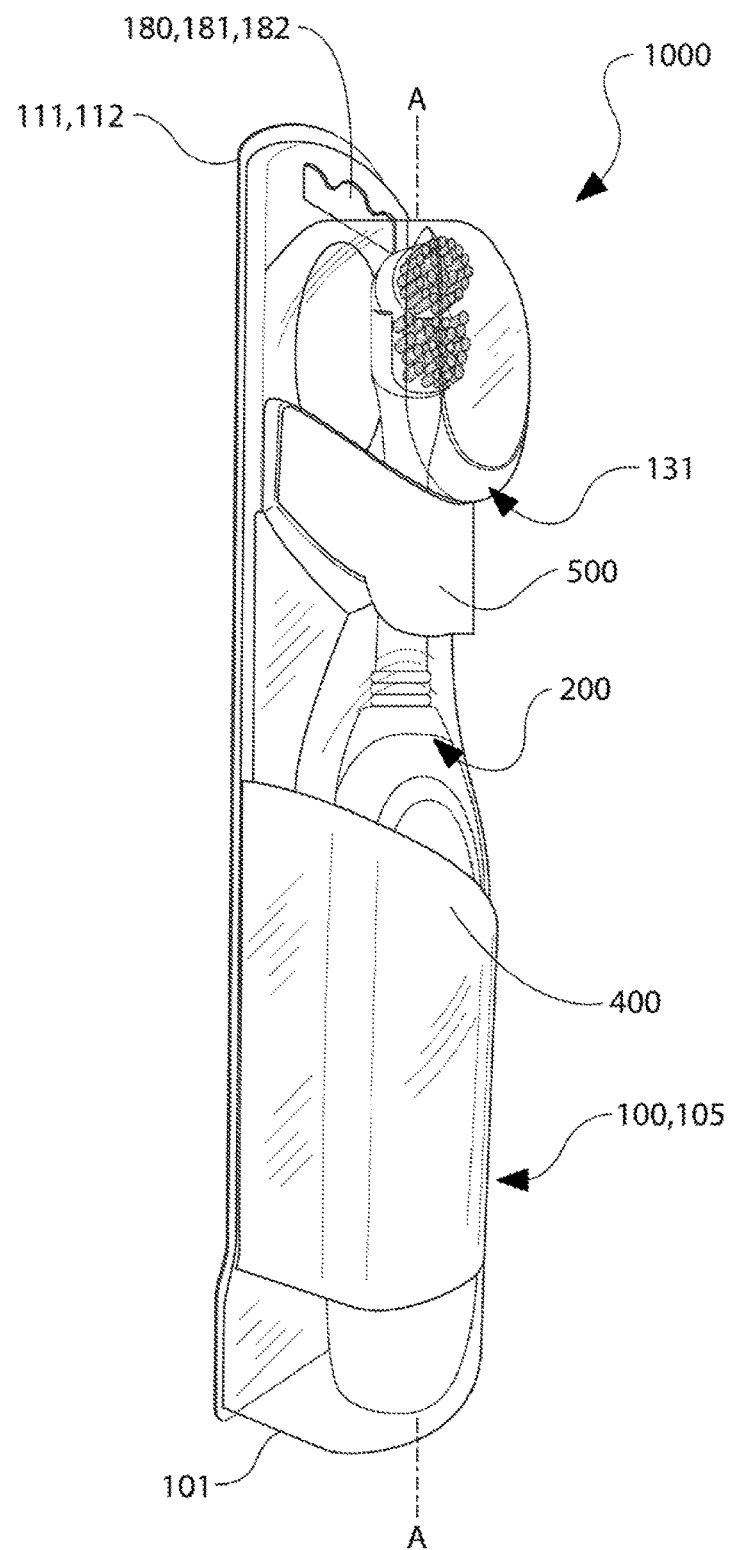
FIG. 1 is a perspective view of a packaged toothbrush according to one embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Figure 2:
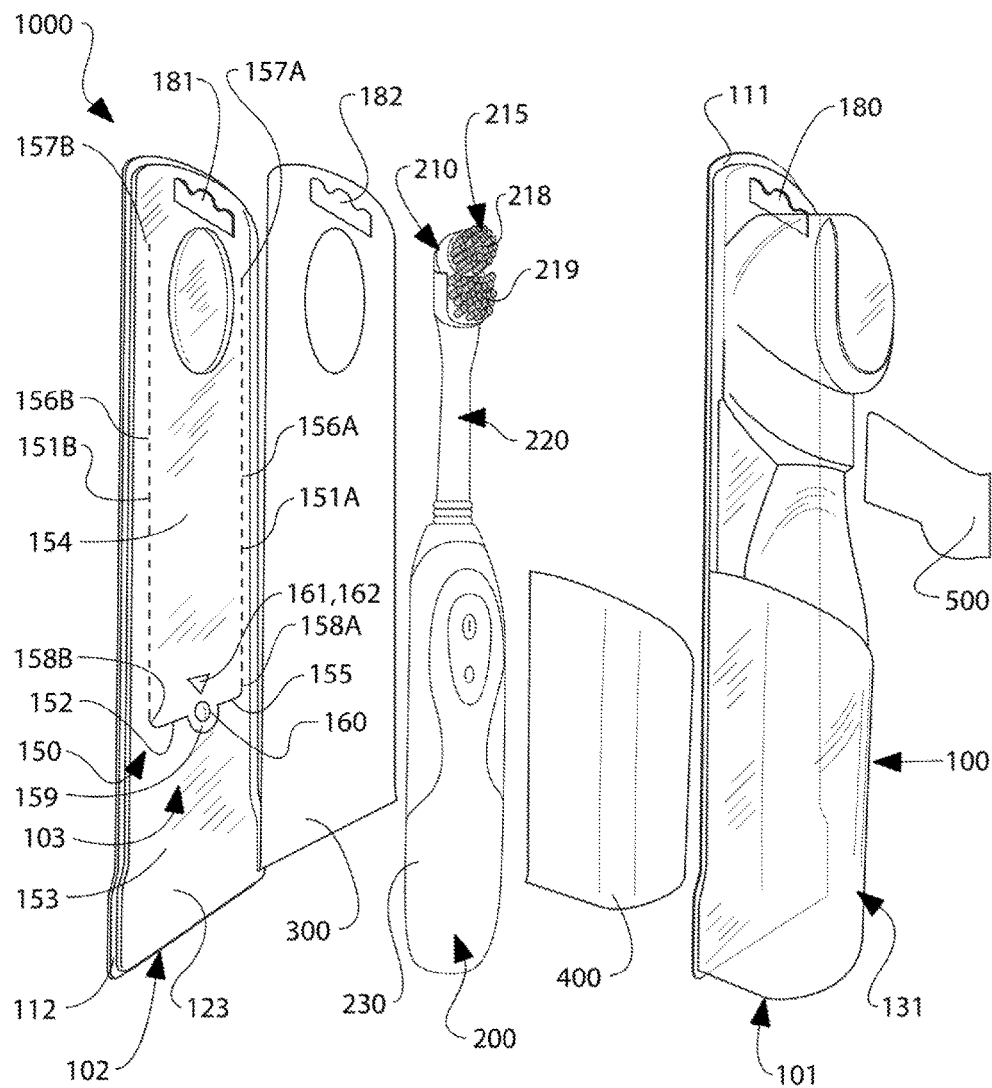
FIG. 2 is a perspective view of the packaged toothbrush of FIG. 1 in an exploded state.

Referring to FIGS. 1-2 concurrently, a packaged toothbrush 1000 is illustrated according to one embodiment of the present invention. The packaged toothbrush 1000 generally comprises a package 100, a toothbrush 200, a backer card 300, a sleeve 400, and a panel 500. In some embodiments, the sleeve 400 may include product information, marketing information, instructions, and/or other relevant information. In the embodiment as shown, the panel 500 is a sticker panel that is attached to a portion of the front cover of the package 100. The panel 500 may include graphics, logos, and/or other visual designs. The toothbrush 200, the backer card 300 and the sleeve 400 are disposed within the package 100. In the exemplified embodiment, the entirety of the toothbrush 200, the entirety of the backer card 300, and the entirety of the sleeve 400 are disposed in the package 100 such that the toothbrush 200, the backer card 300, and the sleeve 400 are sealed therein. However, in alternate embodiments, only a portion of the toothbrush 200, only a portion of the backer card 300 and/or only a portion of the sleeve 400 may be disposed within the package 100 while another portion of the toothbrush 200, the backer card 300, and/or the sleeve 400 protrudes therefrom. Similarly, in alternative embodiments, the entirety of the backer card 300 and the sleeve 400 may be outside of the package 100. In some embodiments, the backer card 300 may form the entirety or a portion of the rear cover of the package 100. In certain embodiments of the invention, the backer card 300, the sleeve 400 and/or the panel 500 may be omitted as desired.

The packaged toothbrush 1000 is exemplified in conjunction with the commercialization of a toothbrush 200. The invention, however, is not so limited. In alternate embodiments, other oral care implements can be used in conjunction with the package 100, including tongue cleaners, tooth polishers, oral care material dispensers, and other oral care ansate implements. Moreover, while the toothbrush 200 is exemplified as a powered toothbrush, the toothbrush 200 may be a manual toothbrush in other embodiments of the invention. Finally, in certain other embodiments, the invention can be the package 100 independent of the product contained therein.

As noted above, in the exemplified embodiment, the toothbrush 200 is a powered toothbrush. In certain embodiments, the toothbrush 200 comprises an oscillating tuft block 218 and a stationary tuft block 219. However, in certain other embodiments the oscillating tuft block 218 may move with a vibratory motion rather than an oscillating motion. Furthermore, in still other embodiments, the toothbrush 200 may comprise one or more movable tuft blocks and the stationary tuft block 219 may be omitted.

The toothbrush 200 generally comprises a head 210, a neck 220 and a handle 230. The handle 230 provides the user with a mechanism by which he/she can readily grip and manipulate the toothbrush 200. The handle 230 may be formed of many different shapes, sizes, materials and a variety of manufacturing methods that are well-known to those skilled in the art. If desired, the handle 230 may include a suitable textured grip made of soft elastomeric material. The handle 230 can be a single or multi-part construction.

The handle 230 transitions into the neck 220 at a distal end. While the neck 220 is illustrated as having has a smaller transverse cross-sectional area than the handle 230, the invention is not so limited. The neck 220 is the transition region between the handle 230 and the head 210 and can conceptually be considered as a portion of the handle 230. In this manner, the head 210 is connected to the distal end of the handle 230 (via the neck 220).

The head 210 generally comprises a front surface, a rear surface and a peripheral surface. The front surface and the rear surface of the head are opposite one another and can take on a wide variety of shapes and contours, none of which are limiting of the present invention. For example, the front and rear surfaces can be planar, contoured or combinations thereof. The rear surface comprises a soft tissue cleanser. The soft tissue cleanser is constructed of an elastomeric material, such as a thermoplastic elastomer, and comprises a plurality of protuberances for engaging and/or massaging soft oral tissue. Details of the soft tissue cleanser are disclosed in U.S. Pat. No. 7,143,462, issued Dec. 5, 2006 to the assignee of the present application, the entirety of which is hereby incorporated by reference. Furthermore, while the head is normally widened relative to the neck of the handle, it could in some constructions simply be a continuous extension or narrowing of the handle.

The front surface of the head comprises a collection of tooth engaging elements 215 extending therefrom for cleaning and/or polishing contact with a user's teeth. While the collection of tooth engaging elements 215 is preferably suited for brushing teeth, the collection of tooth engaging elements 215 can also be used to polish teeth instead of or in addition to cleaning teeth. As used herein, the term "tooth engaging elements" is used in a generic sense to refer to any structure that can be used to clean, polish or wipe the teeth through relative surface contact. Common examples of "tooth engaging elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material preferably has a hardness property in the range of A8 to A25 Shore hardness. One preferred elastomeric material is styrene-ethylene/butylene-styrene block copolymer (SEBS) manufactured by GLS Corporation. Nevertheless, SEBS material from other manufacturers or other materials within and outside the noted hardness range can be used.

When the packaged toothbrush 1000 is assembled for retail display (as shown in FIG. 1), at least a portion of the toothbrush 200 is visible from outside of the package 100 from both the front of the package 100 and the rear of the package 100. As a result, surfaces of the portion of the toothbrush 200 that are substantially opposite one another (i.e., 180° apart) can be viewed by the consumer without removing the toothbrush 200 from the package 100 or compromising the integrity of the package 200.

The package 100 extends along a longitudinal axis A-A. The package 100 may take on a wide variety of embodiments and may be of a wide variety of packaging types as is known in the art. In one embodiment, the package 100 is a blister package. The package 100 generally comprises a body 105, which in the exemplified embodiment is formed by a three-dimensionally contoured front cover 101 and a rear cover 102 that are coupled together. The body 105 comprises a receiving cavity 115 (FIG. 4) in which the toothbrush 200 is contained. While the body 105 is exemplified as being formed of two components, namely the front cover 101 and the rear cover 102, the body 105 may be a single unitary component or it may be formed of more than two components in alternate embodiments of the invention.

The three-dimensionally contoured front cover 110 and the rear cover 102, in one embodiment, are thermoformed plastic films. Suitable thermoformed plastic films may be constructed of such material as polyethyleneterephtalate (PETA, PETG, PETGAG), polyvinylchloride (PVC), polypropylene (PP) or styrol-butadiene-blockcopolymer (SBS), preferred PVC. Other suitable materials of construction for the thermoformed plastic film include, without limitation, renewable primary products, for example of cornstarch, sugar (polyhydroxybutyrat/-valerat), cellulose diacetat, cellulose nitrate, polyactid (PLA), and polyhydroxybutyrat (PHB).

The front cover 101 is three-dimensionally contoured so that a receiving cavity 115 is formed between the front cover 101 and the rear cover 102 when the front cover 101 and the rear cover 102 are coupled together. In one embodiment, the front cover 101 is three-dimensionally contoured to generally correspond to the general shape of the oral care implement that is to be disposed therein, which in the exemplified embodiment is the toothbrush 200. In alternate embodiments, a front cover may be used that is not three-dimensionally contoured if desired. For example, in an alternate embodiment, the front cover may assume a generally rectangular box shape. In the exemplified embodiment, the three-dimensionally contoured front cover 101 comprises a perimeter portion 111 while the rear cover 102 comprises a perimeter portion 112. The perimeter portion 111 of the front cover 101 circumferentially surrounds a three-dimensionally contoured portion 131 of the front cover 110. Similarly, the perimeter portion 112 of the rear cover 102 circumferentially surrounds a panel 103 of the rear cover 102. The perimeter portion 111 of the front cover 101 provides a mating structure for coupling to the perimeter portion 112 of the rear cover 120. The perimeter portion 111 of the front cover 101 can be coupled to the perimeter portion 112 of the rear cover 120 via a thermal weld, adhesive, interference fit, tab, tape, combinations thereof, or any other suitable technique as would be understood by those of skill in the art.

In the exemplified embodiment, the entirety of the front cover 101 and the entirety of the rear cover 102 are substantially transparent, thereby allowing visibility therethrough. However, in alternate embodiments, only a portion of the front cover 101 and a portion of the rear cover 102 may be substantially transparent. As used herein, the term "transparent" includes materials that allow a user to see through the material, even if the material is colored or includes a small degree of translucency.

The front cover 101 further comprises a hanger aperture 180 at a top end thereof. The rear cover 102 also has a corresponding hanger aperture 181 at a top end thereof. The backer panel 300 also comprises such a hanger aperture 182 at a top end thereof. When the package 100 is assembled, the hanger apertures 180-182 are aligned so as to form a passageway through the package 100 which may be used for hanging the packaged toothbrush 1000 for display in a retail store.

The backer card 300, in the exemplified embodiment, is a flat panel. In certain other embodiments, however, the backer card 300 may be three-dimensionally contoured. The backer card 300 may comprise product information. In such embodiments, the backer card 300 comprises indicia that provides information to a consumer about the toothbrush 200 (or other oral care product disposed within the package 100). The indicia on the backer card 300 may include instructions, logos, advertisements, and/or other marketing information. All or a portion of the backer card 300 can be opaque so that product information can be effectively conveyed to the consumer. The backer card 300 can be a single layer or a multi-layer laminate. The backer card 300 can be constructed of plastic, film, paperboard, combinations thereof, or any other suitable material. While the backer card 300 is flexible in certain embodiments, in other embodiments the backer card 300 may be rigid or semi-rigid.

Figure 3:
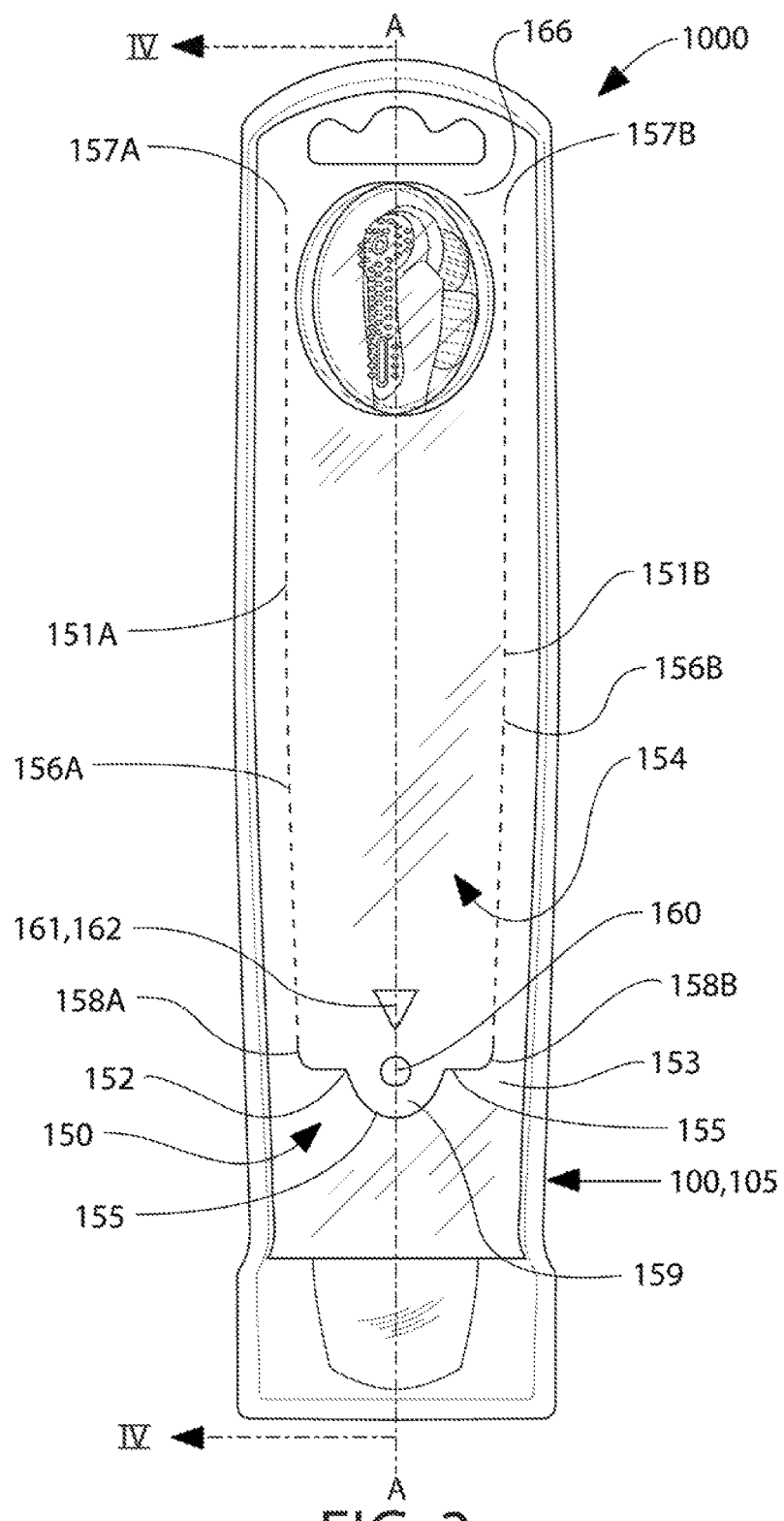
FIG. 3 is a plan rear view of the packaged toothbrush of FIG. 1.
Figure 4:
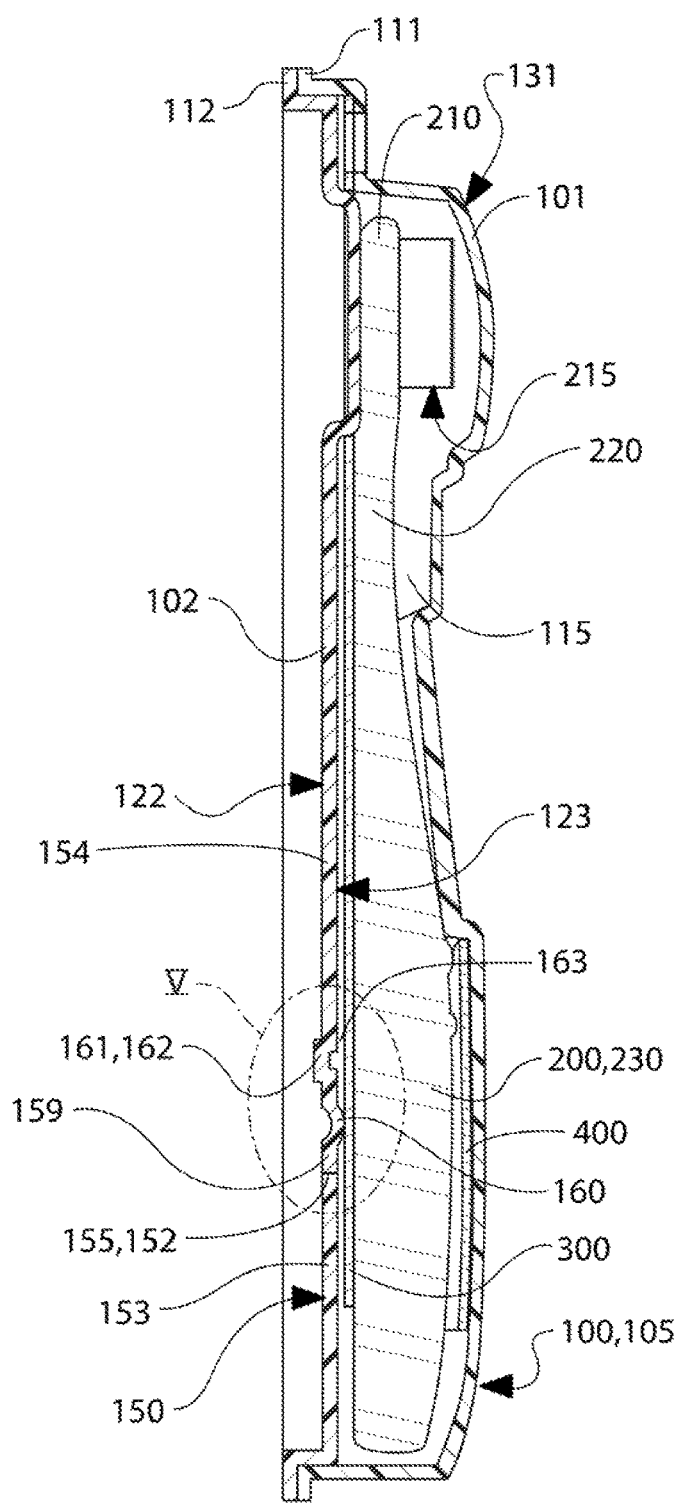
FIG. 4 is a transverse cross-sectional view of the packaged toothbrush of FIG. 1 taken along line IV-IV of FIG. 3.
Figure 5:
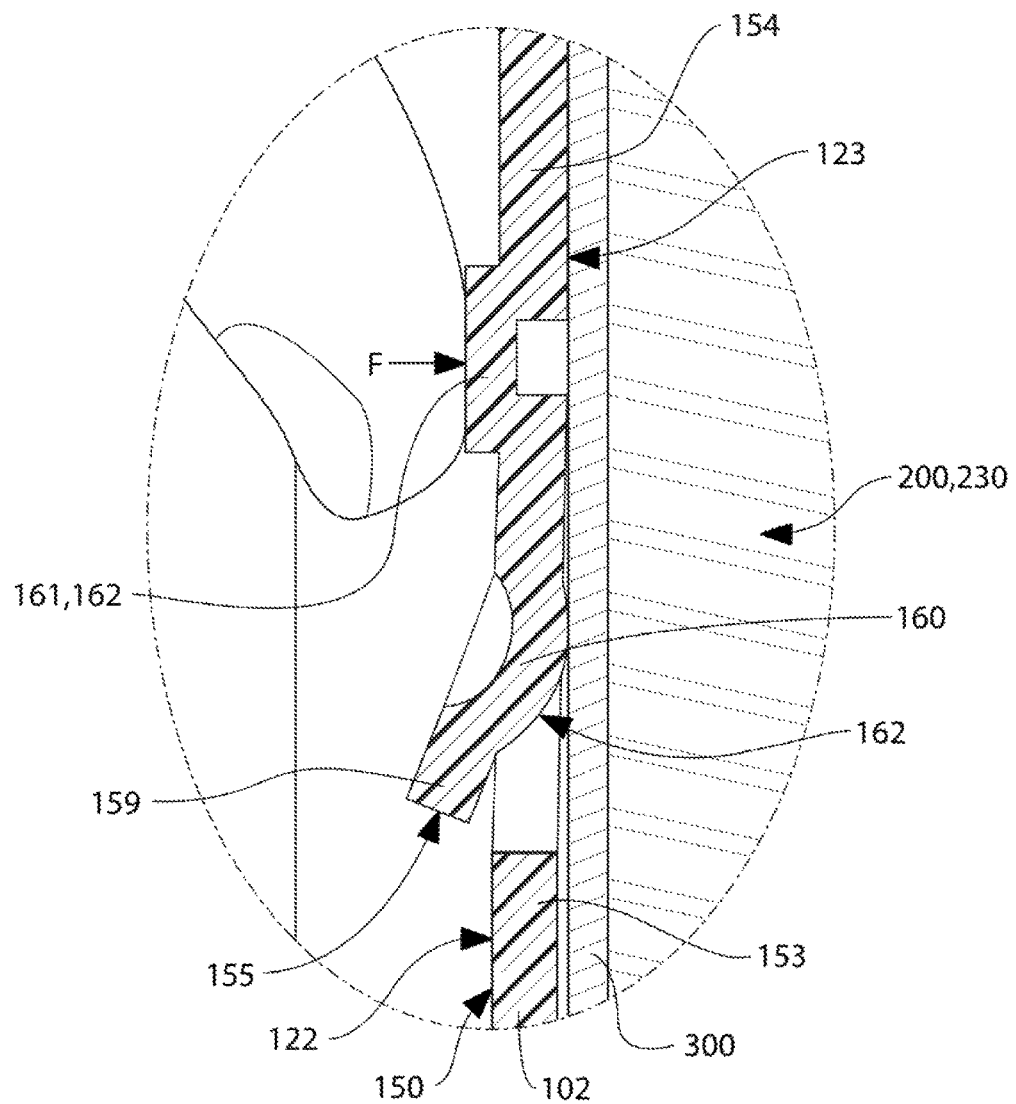
FIG. 5 is a close-up view of area V of FIG. 4, wherein a user has applied a force to the force-application area and the edge of the tear-away portion is protruding from the panel.

Referring now to FIGS. 3-5 concurrently, the easy-open feature of the package 100 will be discussed. The body 105 of the package 100 comprises a panel 150. In the exemplified embodiment, the rear cover 102 comprises the panel 150. However, in alternate embodiments of the invention, the panel 150 (and the associated features discussed below) can be located on the front cover 101 or at any other location on the body 105. In embodiments of the body 105 where additional components/panels are used to form the body 105, the panel 150 can be located on any of such additional components/panels as desired.

The panel 150, in the exemplified embodiment, is a substantially planar panel comprising an outer surface 122 and an inner surface 123. Of course, in other embodiments, the panel 150 may be contoured. The panel 150 comprises a pair of pre-weakened lines 151A-B and a cut 152 that collectively define a base portion 153 and a tear-away portion 154 from the panel 150. As will be discussed in greater detail below, the existence of the pre-weakened lines 151A-B and cut 152 allow the tear-away portion 154 to be separated from the base portion 153 upon the user grasping a portion of the tear-away portion 154 and manually pulling the tear-away portion 154 away from the base portion 153.

In the exemplified embodiment, the cut 152 is an uninterrupted slit that penetrates through the thickness of the panel 150 while the pre-weakened lines 151A-B are linear arrangements of perforations. However, in alternate embodiments, the pre-weakened lines 151A-B can be formed in a wide variety of manners, including without limitation, scoring, pre-creasing, combinations thereof, and/or otherwise comprising the integrity of the panel 150 in a controlled manner through the use of chemical energy, thermal energy, mechanical energy, or combinations thereof. Moreover, while the tear-away portion 154 is defined by a combination of pre-weakened lines 151A-B and a cut 152 in the exemplified embodiment, in other embodiments the tear-away portion 154 may be formed solely by pre-weakened lines or cuts. Furthermore, it is to be understood that the pre-weakened lines 151A-B and/or cuts 152 that define the tear-away portion 154 can take an a wide variety of orientations, arrangements and shapes, thereby allowing the tear-away portion 154 to take on a wide variety of sizes, shapes and/or orientations.

Figure 6:
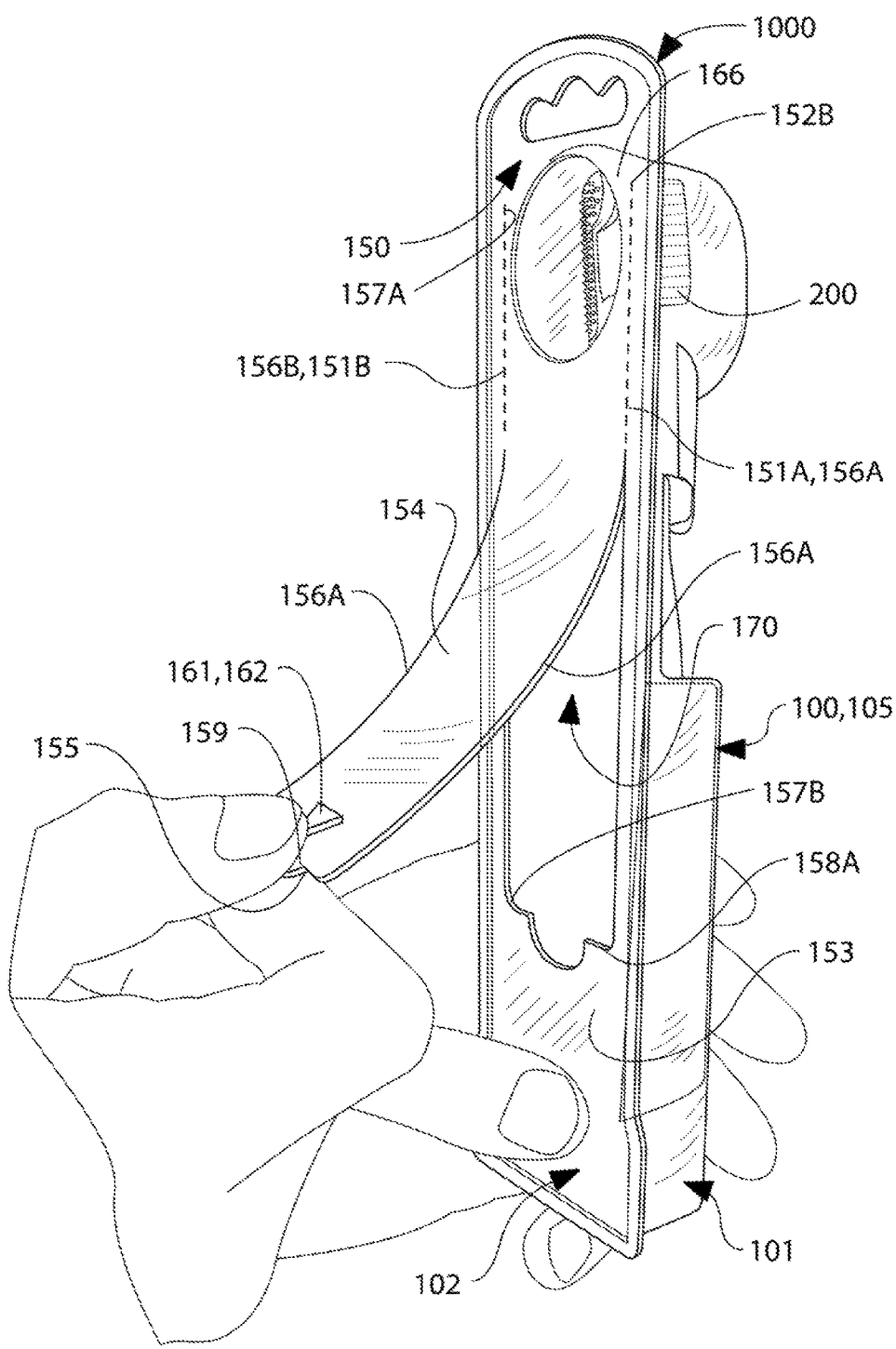
FIG. 6 is a rear perspective view of the packaged toothbrush of FIG. 1 wherein the package has been partially opened in accordance with an embodiment of the present invention.

The tear-away portion 154, as defined by the pre-weakened lines 151A-B and cut 152, comprises a distal edge 155 and a pair of side edges 156A-B (FIG. 6). The distal edge 155 is defined by the cut 152 while the side edges 156A-B are respectively defined by the pre-weakened lines 151A-B. The pre-weakened line 151A extends longitudinally from a proximal end 157A to a distal end 158A. Similarly, the pre-weakened line 151B extends longitudinally from a proximal end 157B to a distal end 158B. In the exemplified embodiment, the pre-weakened lines 151A-B are oriented substantially parallel to one another. Thus, the side edges 156A-B of the tear-away portion 154 are also oriented substantially parallel to one another. Of course, the invention is not limited in all embodiments.

The cut 152 extends transversely between the pre-weakened lines 151A-B, thereby defining the distal edge 155 of the tear-away portion 154. More specifically, the cut 152 extends transversely between the distal ends 157A-B of the pre-weakened lines 151A-B. In alternate embodiment, the cut 152 can be between the pre-weakened lines 151A-B at different locations and/or different orientations.

The cut 152, and thus the distal edge 155, is non-linear and shaped so that a graspable tab 159 is formed into the tear-away portion 154. In the exemplified embodiment, the graspable tab 159 is a rounded portion of the tear-away portion 154 that protrudes from a distal end thereof. Of course, the graspable tab 159 can take on other shapes and sizes in other embodiments of the invention.

The tear-away portion 154 further comprises a protuberance 160 extending from the inner surface 123 of the tear-away portion 154. The protuberance 160 extends from the inner surface 123 and into the receiving cavity 115. In the exemplified embodiment, the protuberance 160 has a convex inner surface 162 (FIG. 5). More specifically, the protuberance 160 is a semi-spherical element in the exemplified embodiment. In other embodiments, the protuberance 160 can take on other shapes, both contoured and not contoured.

The protuberance 160 is located on the tear-away portion 154 so as to be partially located on the graspable tab 159. However, in other embodiments, the protuberance 160 can be located entirely on the graspable tab 159 or entirely outside of the graspable tab 159 as desired. In certain embodiments, the graspable tab 159 may be omitted entirely.

The tear-away portion 154 further comprises a force-application area 161 located adjacent the protuberance 160. The force-application area 161 is that zone/region of the tear-away portion 154 in which it is intended that a user apply a force F to the tear-away portion 154 during opening of the package 100. In the exemplified embodiment, the force-application area 161 comprises a visual indicia 162 to indicate the location of the force-application area 161 on the tear-away portion 154 to the user. In the exemplified embodiment, the visual indicia 162 is a raised feature that protrudes from the outer surface 122 of the tear-away portion 150. In other embodiments, the visual indicia 162 can take the form of a sticker, a contrasting color, a marker, or any other feature that is visually identifiable to the user. In other embodiments, the visual indicia 162 may be omitted all together or provided on the backer panel 300.

Referring now to FIGS. 4-6 concurrently, when force is not applied to the force-application area 161 (as shown in FIG. 4), the distal edge 155 of the tear-away portion 150 (and thus the graspable tab 159) does not protrude from the base portion 153 (or from the rear surface 122 of the panel 150). In the exemplified embodiment, when force is not applied to the force-application area 161, the distal edge 155 of the tear-away portion 150 (and thus the graspable tab 159) lies substantially flush with the base portion 153. This is the natural state of the tear-away portion 150 after manufacture and assembly of the packaged toothbrush 1000, and also the state in which the packaged toothbrush 1000 is sold. Further, in some embodiments, the force-application area 161 may be deformable, i.e., the shape of the force-application area 161 may change when subject to force. In other embodiments, the force-application area 161 may not be deformable. In some other embodiments, the force-application area 161 may be resiliently deformable, i.e., the shape of the force-application area 161 may change when subject to force and may return to its original shape when force is not applied.

When force is not applied to the force-application area 161 (as shown in FIG. 4), a gap 163 exists between the inner surface 123 of the panel 150 and the backer panel 300 in the location of the force-application area 161. The protuberance 160 is located at an axial position between the distal edge 155 of the tear-away portion 154 and the force-application area 161. This allows the protuberance 160 to act as a fulcrum that forces the distal edge 155 of the tear-away portion 154 (and thus the graspable tab 159) to protrude from the base portion 153 (and the outer surface 122 of the panel 150) when a force F is applied to the force-application area 161 (as shown in FIG. 5). The convex inner surface 162 of the protuberance 160 promotes the fulcrum effect. It is understood that the force F may be applied to other area, i.e., an outer surface, of the tear-away portion 154 in other embodiments.

The protuberance 160 is aligned with the handle portion 230 of the toothbrush 200. When the force F is applied to the force-application area 161 of the tear-away portion 154, the protuberance 160 is forced inward into the receiving cavity 115 and against the backer panel 300, which is in turn in contact with (or immediately comes into contact with) the handle portion 230 of the toothbrush 200. As a result, the handle portion 230 of the toothbrush 200 acts as a foundation for the fulcrum/protuberance 160 when the force F is applied to the force-application area 161, thereby forcing a pivoting motion about the protuberance 160 that causes the distal edge (and thus the graspable tab 159) to protrude from the base portion 153 (and the outer surface 122 of the panel 150), which is shown in FIG. 5. Concurrently therewith, the tear-away portion 154, in the location of the force-application area 161, bends inward, thereby eliminating the gap 163. Of course, the backer panel 300 can be omitted in certain embodiments, allowing the inner surface 122 of the tear-away portion 154 in the location of the force-application area 161 to come into direct contact with the handle portion 230 of the toothbrush 200.

Once the force F is applied to the force-application area 161 (or other area) of the tear-away portion 154 and the distal edge 155 (including the graspable tab 159) protrude from the base portion 153, the user can easily grasp the protruding portion of the tear away panel 154, which in the exemplified embodiment is the graspable tab 159. In other embodiments, the protruding portion may merely be a distal portion of the tear-away portion 154 adjacent the distal edge 155. Once the user has grasped the graspable tab 159, he/she pulls outward, thereby causing the tear-away portion 154 to be severed from the base portion 153 along the pre-weakened lines 151A-B. As the tear-away portion 154 is severed from the base portion 153 along the pre-weakened lines 151A-B, the tear-away portion 154 is pulled out of plane with respect to the base portion 153, thereby exposing the side edges 156A-B of the tear-away portion 154. As a result an access opening 170 is formed that allows the toothbrush 200 to be removed from the package 100.

However, because the panel 150 is free of any pre-weakened lines and/or cuts between the proximal ends 157A-B, the tear-away portion 154 is not free to be completely separated from the base portion 153. Rather, in the exemplified embodiment, a living hinge 166 is formed in the panel 150 between the proximal ends 157A-B of the pre-weakened areas 157A-B. As a result, the tear-away portion 154 is a hinged panel that pivots about the living hinge 166.

Thus, the tear-away portion 154 remains connected to the base portion 153 via the living hinge at the proximal end of the tear-away portion 154. In alternate embodiments of the invention, the tear-away portion 154 may be completely separable from the base portion 153.

Finally, while the protuberance 160 is exemplified as being part of and extending from the tear-away portion 154, the invention is not so limited. In alternate embodiments, the protuberance 160 can be located on the back panel 300 or even on the toothbrush 200 is itself. In certain other embodiments, the protuberance 160 can be a separate insert or component (or a part thereof) that is strategically positioned within the receiving cavity 115.

Figure 7:
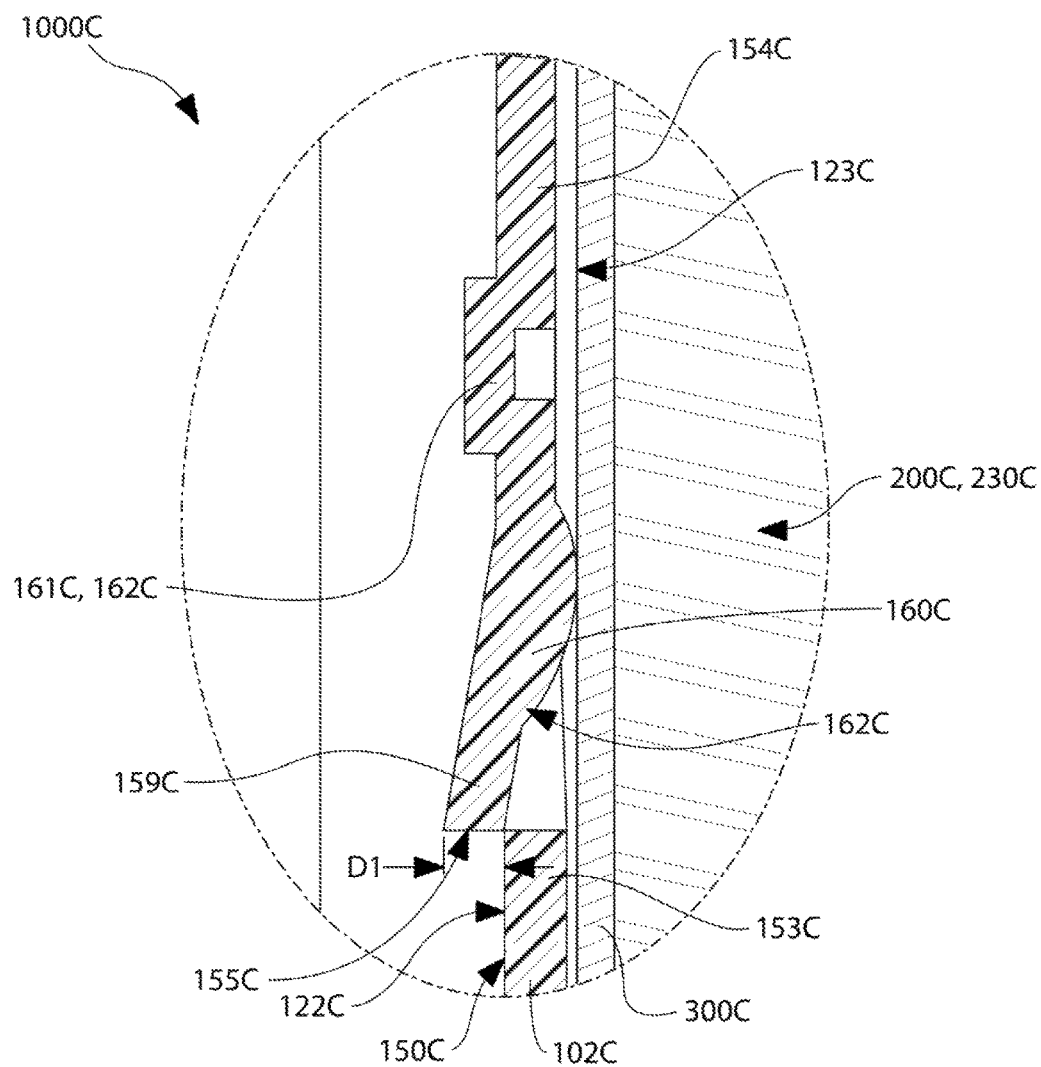
FIG. 7 is a close-up view of a transverse cross-section of a portion of a packaged toothbrush according to a second embodiment of the present invention, wherein the edge of the tear away portion protrudes a first distance from the base portion in a natural (i.e., unforced) state.
Figure 8:
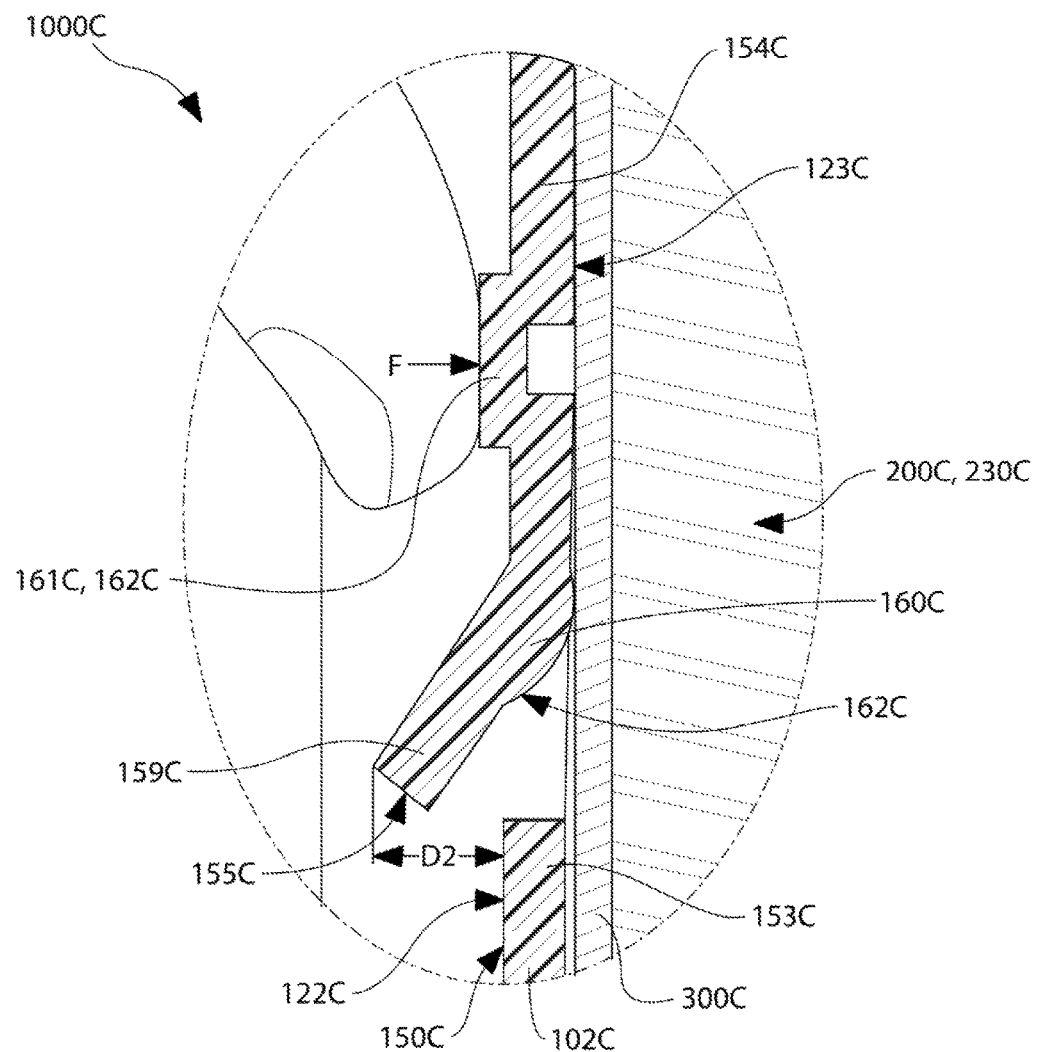
FIG. 8 is a close-up view of the portion of the packaged toothbrush of FIG. 8, wherein the edge of the tear away portion protrudes a second distance from the base portion when a force is applied to a force indication area, the second distance being greater than the first distance.

Referring now to FIGS. 7-8 concurrently, a second embodiment of a packaged toothbrush 1000C according to the present invention is illustrated. The second embodiment of the packaged toothbrush 1000C is identical to the packaged toothbrush 1000 of FIGS. 1-6 (discussed above) with the exception that the panel 150C is constructed so that the distal edge 155C of the tear-away portion 154C protrudes outwardly from the base portion 153C a first distance D1 when no force is being applied to the force-application area 161C, rather than being substantially flush with the base portion 161C, as is the case with the embodiment of FIGS. 1-6. In other word, the embodiment of FIGS. 1-6 may be considered as an example of the embodiment of FIGS. 7-8 where the first distance D1 is zero. All other structural elements (and their function) of the second embodiment of the packaged toothbrush 1000C (including the package and the toothbrush) are identical to the first embodiment of the packaged toothbrush 1000 discussed in FIGS. 1-6, and are hereby incorporated by reference. Corresponding elements are given identical numbers with the addition of a "C" alphabetical suffix. Thus, it is to be understood that above-referenced description of the remaining structure FIGS. 1-6 is applicable to the second embodiment of the packaged toothbrush 1000C.

As shown in FIG. 7, the distal edge 155C of the tear away portion 154C of the panel 150C protrudes a first distance D1 from the base portion 153C of the panel 150C even though no force is being applied to the force-application area 161C. This allows the consumer to more easily identify and recognize the existence of the easy open function. A gap 163C still exists between the inner surface 123C of the panel 150C and the backer panel 300C in the location of the force-application area 161C. The protuberance 160C is located at an axial position between the distal edge 155C of the tear-away portion 154C and the force-application area 161C. As with the embodiment of FIGS. 1-6, this allows the protuberance 160C to act as a fulcrum that forces the distal edge 155C of the tear-away portion 154C (and thus the graspable tab 159C) to further protrude from the base portion 153C (and the outer surface 122C of the panel 150C) when a force F is applied to the force-application area 161C (as shown in FIG. 8). The convex inner surface 162C of the protuberance 160C promotes the fulcrum effect.

As shown in FIG. 8, the protuberance 160C is aligned with the handle portion 230C of the toothbrush 200C. When the force F is applied to the force-application area 161C of the tear-away portion 154C, the protuberance 160C is forced inward into the receiving cavity 115C and against the backer panel 300C, which is in turn in contact with (or immediately comes into contact with) the handle portion 230C of the toothbrush 200C. As a result, the handle portion 230C of the toothbrush 200C acts as a foundation for the fulcrum/protuberance 160C when the force F is applied to the force-application area 161C, thereby forcing a pivoting motion about the protuberance 160C that causes the distal edge 155C (and thus the graspable tab 159) to protrude a second distance D2 from the base portion 153C (and the outer surface 122C of the panel 150C). The second distance D2 is greater than the distance D1. Concurrently therewith, the tear-away portion 154C, in the location of the force-application area 161C, bends inward, thereby eliminating the gap 163C. Of course, the backer panel 300C can be omitted in certain embodiments, allowing the inner surface 122C of the tear-away portion 154C in the location of the force-application area 161C to come into direct contact with the handle portion 230C of the toothbrush 200C.

Once the force F is applied to the force-application area 161C of the tear-away portion 154C and the distal edge 155C (including the graspable tab 159C) protrude from the base portion 153C, the user can easily grasp the protruding portion of the tear away panel 154C, which in the exemplified embodiment is the graspable tab 159C. In other embodiments, the protruding portion may merely be a distal portion of the tear-away portion 154C adjacent the distal edge 155C.

Finally, while the protuberance 160C is exemplified as being part of and extending from the tear-away portion 154C, the invention is not so limited. In alternate embodiments, the protuberance 160C can be located on the back panel 300C or even on the toothbrush 200C is itself. In certain other embodiments, the protuberance 160C can be a separate insert or component (or a part thereof) that is strategically positioned within the receiving cavity 115C.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. A packaged oral care implement comprising;
   a blister package comprising:
      a receiving cavity;
      a panel, the panel comprising a tear-away portion and a base portion, the tear-away portion comprising an edge protruding outwardly a first distance from the base portion;
      a protuberance extending from an inner surface of the tear-away portion; and
      the edge protruding outwardly a second distance from the base portion when a force is applied to an outer surface of the tear-away portion as a result of the protuberance acting as a fulcrum, the second distance greater than the first distance: and
   an oral care implement positioned within the receiving cavity.

2. The packaged oral care implement according to claim 1 wherein:
   the blister package further comprising a force-application area; and
   the protuberance is located between the edge and the force-application area.

3. The packaged oral care implement according to claim 1, wherein when the force is applied to an outer surface of the tear-away portion, the three is applied to the force-application area.

4. The packaged oral care implement according to claim 3 wherein a portion of the oral care implement lies directly beneath the protuberance and acts as a foundation for the fulcrum when the force is applied to the force-application area.

5. The packaged oral care implement according to claim 1, wherein the tear-away portion comprises a graspable tab at the edge.

6. The packaged oral care implement according to claim 5 wherein the protuberance is located at least partially on the graspable tab.

7. The packaged oral care implement according to claim 3, wherein the force-application area comprises visual indicia for identifying the existence of the force-application area.

8. The packaged oral care implement according to claim 7 wherein the visual indicia comprises a raised feature that protrudes from an outer surface of the tear-away portion.

9. The packaged oral care implement according to claim 1, wherein the panel comprises a pair of spaced apart pre-weakened lines and a cut extending between distal ends of the pre-weakened lines, the cut defining the edge of the tear-away portion, and the pre-weakened lines and the cut collectively defining the tear-away portion.

10. The packaged oral care implement according to claim 1, wherein the tear-away portion is connected to the base portion via a living hinge at a proximal end of the tear-away portion.

11. The packaged oral care implement according to claim 1, wherein the blister package comprises a front cover and a rear cover coupled together to form the receiving cavity, and wherein the front cover and the rear cover are thermo-formed plastic films.

12. The packaged oral care implement according to claim 1 wherein the front cover comprises a three-dimensional contour.

13. The packaged oral care implement according to claim 12 wherein the three-dimensional contour generally corresponds in shape to the oral care implement.

* * * * *